United States Patent [19]
Holtermann

[11] Patent Number: 5,667,502
[45] Date of Patent: Sep. 16, 1997

[54] INFLATABLE COLLECTING BAG, IN PARTICULAR FOR AN ARTIFICIAL ANUS

[75] Inventor: Henri Holtermann, Saint-Jean-de-Luz, France

[73] Assignee: B. Braun Biotrol, Boulogne, France

[21] Appl. No.: 608,080

[22] Filed: Feb. 28, 1996

[30] Foreign Application Priority Data

Mar. 1, 1995 [FR] France .................. 95 02359

[51] Int. Cl.⁶ .................... A61F 5/44
[52] U.S. Cl. .......... 604/342; 604/332; 604/327; 604/349
[58] Field of Search ............... 604/327–332, 604/338–342, 349–352

[56] References Cited

U.S. PATENT DOCUMENTS

| 3,902,496 | 9/1975 | Eakin . |
| 4,319,571 | 3/1982 | Winchell . |
| 4,710,182 | 12/1987 | Bryson . |

FOREIGN PATENT DOCUMENTS

| A 0 245 064 | 11/1987 | European Pat. Off. . |
| A 0 248 657 | 12/1987 | European Pat. Off. . |
| A 0 408 296 | 1/1991 | European Pat. Off. . |
| 2 139 501 | 11/1984 | United Kingdom . |
| WO92/18074 | 10/1992 | WIPO . |

OTHER PUBLICATIONS

French Search Report.

*Primary Examiner*—Robert A. Clarke
*Attorney, Agent, or Firm*—Morrison & Foerster LLP

[57] ABSTRACT

The present invention relates to a collecting bag in particular for collecting body excreta running from an artificial anus, the bag being provided with padding designed, when the bag is in place, to surround the artificial anus in order to protect it. The padding is constituted by a cushion adapted to be inflated, and inflation means are also provided to enable the patient to inflate the cushion to the desired extent. In order to avoid excessively reducing the volume of excreta that can be collected, the cushion preferably extends along the periphery of the bag. It is also preferably disposed between the front wall and the back wall of the bag so as to hold them apart from each other. In this way, excreta, including solid excreta, have no difficulty in penetrating into the bag as stiffened by the inflated cushion, which thus transforms the bag into a kind of box.

15 Claims, 4 Drawing Sheets

INFLATABLE COLLECTING BAG, IN PARTICULAR FOR AN ARTIFICIAL ANUS

The present invention relates to a bag for collecting body excreta and/or for draining a wound, and more particularly to a bag for collecting matter running out from an artificial anus.

BACKGROUND OF THE INVENTION

With certain disorders, it is necessary to perform a surgical operation that consists in removing the downstream portion of the patient's intestine. The end of the portion of the intestine left in place is then brought out through the skin of the abdomen to constitute an artificial anus. However, under such circumstances, the patient can no longer control evacuation of matter. A collecting bag is thus placed at the artificial anus to receive matter as it flows out and to store it.

The bags most widely used at present include an adhesive base plate with a central opening. The base plate is attached to the bag so that its opening faces an opening of the bag that is formed in its back wall (i.e. the wall next to the skin). To keep the bag in place, the patient sticks the base plate to the skin around the artificial anus so that the anus is within the opening of the base plate, and is thus in communication with the inside of the collecting bag which can then receive matter.

In certain "one-piece" models of bag, the base plate is merely welded to the bag. In other, "two-piece" models, the base plate and the bag are adapted to be connected together by means of a coupling which can be opened and closed. That serves, in particular, to allow the base plate to remain in place while the bag is removed, e.g. to be changed.

Either way, wearing such bags can be painful. They are pressed relatively closely against the abdomen by clothing, and movements of the patient inevitably give rise to pushing and pulling on the artificial anus which often presents as an open wound. Efforts have therefore been made to provide such bags with padding to improve comfort.

One known form of bag is described in application EP 0 408 296. Its walls are constituted by a multilayer film of structure comparable to that of the bubble sheets lining the insides of padded envelopes. At regular intervals, the outer layers of the film are spaced apart from the inner layers so as to define air-filled cells or "bubbles" between them which project around the bag. As a result, the bag touches the skin of the patient only over the bubbles, thereby correspondingly reducing the area of contact with the skin and the resulting discomfort.

Another known form of bag is described in application GB 2 139 501. Its front wall (clothing side) and its back wall (skin side) are separated internally by an intermediate wall that is impermeable to liquids, but permeable to gases. This prevents the collected matter that penetrates through the opening in the back wall of the bag from coming into contact with the front wall. However it does allow gases to pass to the front wall which includes a vent filter. There is thus no risk of the filter becoming clogged with matter. In one embodiment, the intermediate wall occupies only the top portion of the bag and its bottom edge is welded to the front wall of the bag. Advantageously, foam is disposed in the chamber made in this way. That application specifies that the foam then acts as padding, making the bag more comfortable.

The drawback of those known forms of bag is that the bag is also padded around the artificial anus. This gives rise to pressure, in particular pressure exerted by clothing, that bears directly on the artificial anus, even if it does so through padding and is therefore somewhat damped.

Another known form of bag is described in patent U.S. Pat. No. 3,902,496 which mitigates the above drawback by avoiding pressure being applied directly to the artificial anus. To this end, it includes two cushions both extending vertically and situated on either side of the opening of the bag. The cushions are advantageously formed in an intermediate wall of the bag which is folded over and welded. They may be filled with air at atmospheric pressure, for example.

A drawback of the above known form of bag, that also applies to the preceding forms, is that the thickness of the padding cannot be changed. Unfortunately, the shape of an artificial anus can vary widely between patients. Some patients, e.g. having an invaginated anus, will want considerable thickness of padding, while others will want little extra thickness.

OBJECT AND SUMMARY OF THE INVENTION

The object of the present invention is to mitigate this drawback by means of a collecting bag having padding means whose thickness can be adapted to the artificial anus of the patient. This adaptability must also be achieved without making the bag excessively expensive to produce.

For this purpose, the invention provides a collecting bag in particular for collecting body excreta running from an artificial anus, the bag being provided with padding designed, when the bag is in place, to surround the artificial anus and capable of preventing pressure, in particular as exerted by clothing, from bearing against said artificial anus, wherein the padding is constituted by a cushion adapted to be inflated, and wherein inflation means are also provided for inflating the cushion. Said means enable the patient to inflate the cushion as desired. It is also preferable for the inflation means to allow deflation in case the patient finds that the cushion has been over-inflated.

Advantageously, the inflation means comprise a non-return valve having at least a portion inside the cushion. In which case the patient can use a gas refill. It is also possible to use a syringe for forcing air into the cushion. However it is even more convenient for the valve also to have an outside portion adapted to receive an end piece, enabling a user to blow air therein for the purpose of inflating the cushion.

For example, the valve is formed by two walls that are flexible and impermeable to gas, that face each other, that are welded together laterally, and that are provided with means for stiffening the walls of the valve transversely so that the walls are pressed against each other in airtight manner under the effect of the pressure that exists inside the cushion. The means for stiffening the walls of the valve transversely are then preferably constituted by a transverse weld between the walls of the valve, a passage being formed through the transverse weld to provide communication between the cushion and the outside. It is easy to provide the passage, in particular by interposing a metal rod between the two walls of the valve and, for example, hot pressing the entire width of the walls in order to weld them together transversely.

In another example, the valve is formed by two rigid pieces that terminate at the end of the valve inside the cushion in sufficiently tapering manner to enable them to be pressed against each other in airtight manner by the pressure that exists inside the cushion. Such valves are commercially available.

When the bag includes a receptacle for receiving and storing excreta, the receptacle having a periphery, and also having an inlet opening for excreta, and being adapted to be held on a patient in such a manner that the opening is in register with the artificial anus, it is preferable for the cushion to extend from the periphery of the receptacle to an outline of the cushion situated at a sufficient distance from the opening to ensure that the swelling formed by the inflated cushion does not transmit pressure to the artificial anus. This ensures firstly that the bag itself does not bear against the artificial anus. Also, the back wall of the receptacle facing the skin immediately around the anus is not pressed against the abdomen by the cushion. The corresponding clearance can give relief to a relatively painful zone. Further, positioning the cushion along the periphery of the bag maximizes the volume of excreta that can be collected.

When the receptacle is constituted by a back wall in which the opening of the receptacle is formed, and by a front wall overlying the back wall, it is preferable for the cushion to be disposed between the front and back walls. As a result, the inflated cushion spaces the front and back walls apart from each other. That is advantageous for ensuring that the excreta inlet is not obstructed by the front wall of the receptacle sticking to the back wall. In fact, the cushion provides a tensioning effect on the walls, thereby stiffening the bag and transforming it into a kind of box into which excreta, even when solid, can pass without impediment.

More practically, when the front and back walls are welded together along a peripheral weld which defines the periphery of the receptacle, the cushion is advantageously constituted by two walls that are flexible and impermeable to gas, that face each other, and that are welded together at the peripheral weld and also along an inside weld following the outline of the cushion. A third wall that is flexible and impermeable to gas can then have both edges engaged in the peripheral weld of the receptacle so as to form a bellows. This makes a larger inflation volume possible, and also causes the front and back walls of the bag to be put under tension. A box is thus formed into which excreta, and more particularly solid feces, can move better down to the bottom of the bag.

Still in more practical manner, when the front and back walls are welded together along a peripheral weld which defines the periphery of the receptacle, the cushion is advantageously constituted by a wall that is flexible and impermeable to gas, and that is welded to the back wall of the receptacle at the peripheral weld and also along an internal weld following the outline of the cushion. A wall fewer is thus required to form the cushion.

In this case, the wall constituting the cushion is an intermediate wall of the receptacle which is welded to the front and back walls along the entire peripheral weld, and also to the back wall along an additional weld surrounding the inlet opening for excreta so that the excreta is stored solely between the front wall and the intermediate wall. This structure makes manufacture possible merely by stacking films which are welded and cut out together without any need to ensure that the various elements making up the bag are aligned in a particular manner. It is much cheaper. Where appropriate, the intermediate wall includes at least one fold adapted to form a bellows in the cushion so as to make a greater inflation volume possible and so as to tension the walls of the bag.

Once placed on the patient, the receptacle presents a top portion and a bottom portion, and advantageously the cushion extends in at least the top portion of the receptacle. The inflated cushion has a certain amount of stiffness. Its presence at the top of the bag prevents the front wall from sagging under the weight of matter accumulated in the bottom of the receptacle of the bag. In which case, it is advantageous to dispose the vent filter on the front wall of the receptacle at the same height as the cushion, since the cushion then prevents the filter becoming obstructed by excreta or indeed by the back wall of the receptacle.

BRIEF DESCRIPTION OF THE DRAWINGS

The invention will be better understood on reading the following detailed description and on examining the accompanying drawings which show embodiments of the invention as non-limiting examples. In the drawings.

MORE DETAILED DESCRIPTION

Figure 2:
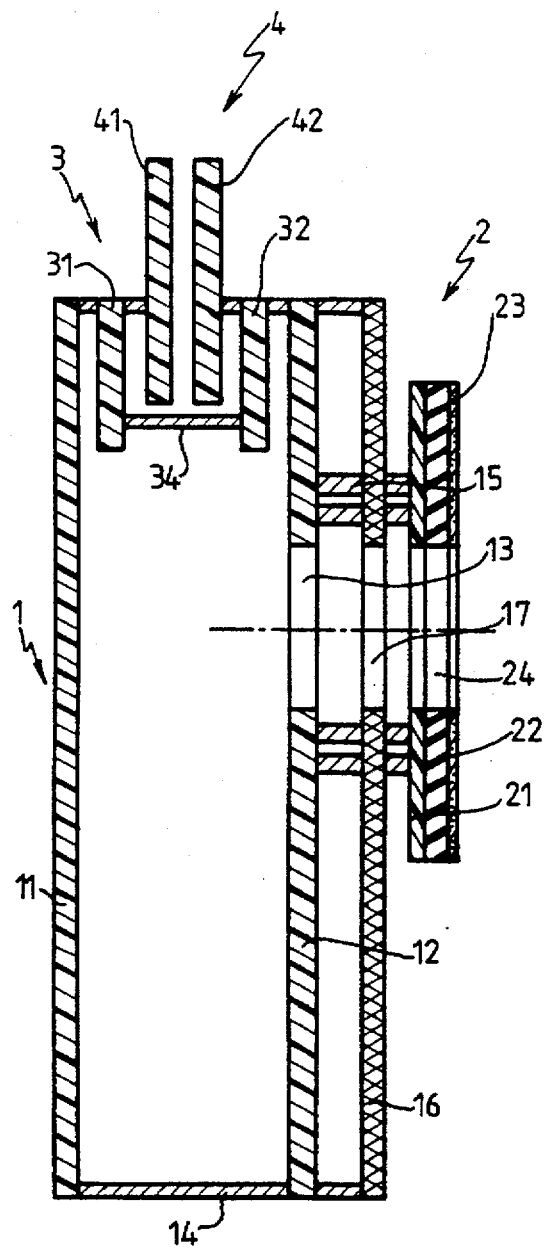
FIG. 2 is a section on the axis of symmetry I—I of the embodiment of the bag shown in FIG. 1, the section being an exploded view.

In the drawings, elements of the various embodiments which are equivalent have been given identical reference numerals. Compared with their real size, the exploded sections exaggerate the thickness of the various walls of the collecting bags, of the layers of their base plates, and in particular of the welds interconnecting those elements. In fact, the walls are thin films comprising a single layer or a plurality of layers and they are made out of thermoplastic materials. They are about one-tenth of a millimeter thick. The welds are made by hot pressing, high frequencies, or ultrasound, and their thicknesses may be even smaller. They are indicated in the drawings, and in particular in the front views, by strips of shading. The sections are exploded in order to distinguish clearly the various elements of the bags. Finally, the walls are drawn as though transparent so that the elements situated at the back of the bag are shown as being visible. In practice, this is often the case so as to facilitate checking the extent to which they have been filled up in use.

Figure 1:
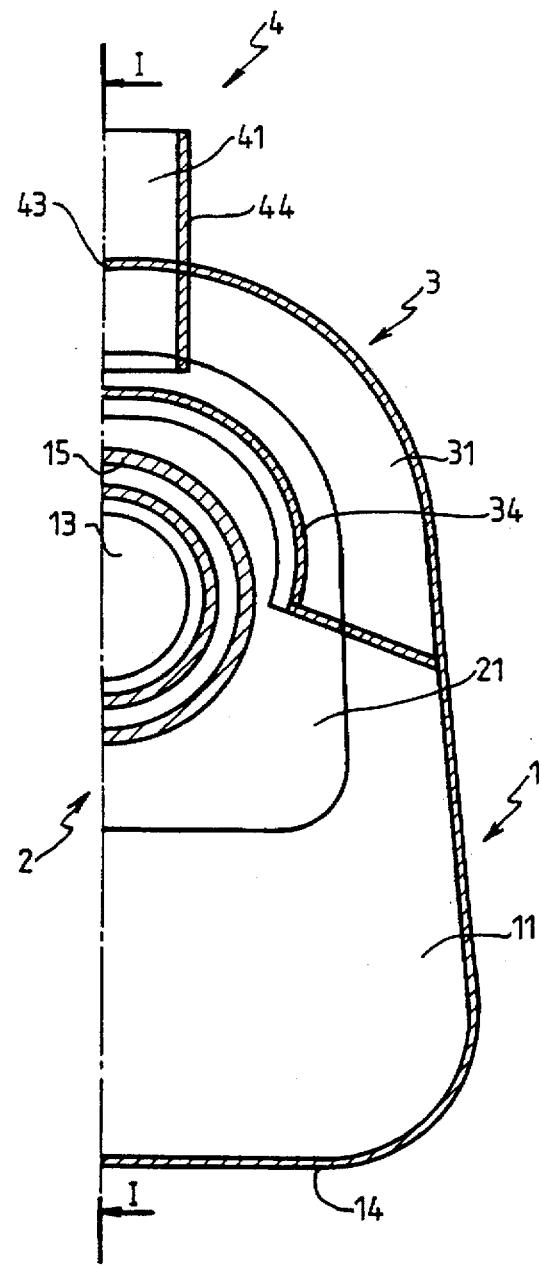
FIG. 1 is a fragmentary front view of a first embodiment of a collecting bag of the invention, with only half of the bag being shown, the half that is not drawn being symmetrical about the axis I—I of the half shown.

A first embodiment of a collecting bag of the invention is shown in part in the front view of FIG. 1 and in the exploded section of FIG. 2. It comprises firstly a receptacle 1 for receiving and storing matter. In known manner, it comprises two walls 11 and 12 which face each other and which are held together in sealed manner by a peripheral weld 14. Although not essential in the context of the present invention, the walls are shown in the drawings as being trapezium-shaped with rounded edges. The bag is worn so that the small side of the trapezium is at the top. There is then a wall 11 that comes into contact with clothing—referred to herein as the "front" wall—and a wall 12 which is in contact with the skin—referred to herein as the "back" wall. In fact, direct contact between the back wall 12 and the skin is usually avoided because of the risk of overheating due in particular to sweating. A coating 16 is secured to the outside of the back wall 12. For this purpose, it may be welded to the walls 11 and 12 at the peripheral weld 14. The coating is advantageously made of non-woven fabric.

In the top half of the back wall 12, there is provided an inlet opening 13 for matter. When there is a coating 16, it also includes an opening 17 that coincides with the opening 13 of the back wall 12. A base plate 2 for fixing the bag to the patient is secured to the outside of the bag, in register with the openings. The base plate 2 itself includes an opening 24 which coincides with the openings 13 and 17 and which is designed to receive the artificial anus. In this embodiment of the bag, the base plate 2 is secured in known manner both to the back wall 12 and to the coating 16 by means of one or more concentric welds 15 surrounding the openings.

In known manner, the base plate 2 itself comprises a relatively thick adhesive layer 22 (about one millimeter thick) applied to a substrate 21 and preferably protected by a peel-off sheet 23. The adhesive layer 22 is made of an adhesive substance which is generally mixed with a large quantity of hydrocolloides. These are capable of absorbing the moisture given off by the skin, or by the matter. The base plate 2 thus manages to remain stuck around the artificial anus at least for the time required to fill the bag.

In a manner specific to the present invention, the collecting bag also includes a cushion 3. In the embodiment of FIGS. 1 and 2, the cushion 3 is crescent-shaped, fitting around the top edge of the bag. For this purpose, it is made from two walls 31 and 32 that face each other and that are interconnected on top by the peripheral weld 14 of the receptacle 1 and at the bottom by another weld 34. The walls 31 and 32 may be made out of material identical to that used for making the walls 11 and 12 of the receptacle, however that is not essential. It is sufficient merely for them to be made out of a material that is flexible and that is impermeable to gas. The cushion 3 is designed to be inflated with air. When inflated, the walls 31 and 32 must be capable of deforming to form a kind of swelling.

When the bag is fixed to the patient, the swelling is intended to extend around the top portion of the artificial anus. Since matter soon begins to accumulate in the bottom portion of the bag, the anus is more or less completely surrounded by padding capable of damping the transmission of pressure, in particular from clothing, and of preventing the pressure bearing directly against the anus.

The cushion 3 is inside the receptacle. Thus, when inflated, it spreads the front and back walls 11 and 12 apart from each other. This has the particular advantage of preventing the immediate surroundings of the inlet opening 13 for matter remaining stuck to the front wall 11, which would make it difficult for matter to penetrate any further into the receptacle 1.

This has another advantage of preventing the portions of the walls 11 and 12 of the receptacle 1 that are above the inlet opening 13 for matter from sagging forwards under the weight of matter accumulating in the bottom of the bag. Once inflated, the cushion 3 imparts a certain amount of stiffness to the top portion of the receptacle 1.

In a manner that is likewise specific to the present invention, an inflation valve 4 is provided to enable the patient to inflate the cushion 3 to the desired extent. In the embodiment of the bag shown in FIGS. 1 and 2, the valve 4 occupies the top portion of the bag. It comprises two walls 41 and 42 that face each other and that are connected together by two lateral welds 44. The walls 41 and 42 may be made out of material identical to that used for making the walls 11 and 12 of the receptacle. However that is not essential. It suffices for the material to be flexible and impermeable to gas.

In order to put the cushion 3 into communication with the outside, the walls 41 and 42 pass through the peripheral weld 14 of the receptacle 1. In fact, they are also welded together along the weld 14 except at a narrow passage 43, e.g. centered on the axis of symmetry I—I. A simple way of obtaining such a passage 43 consists in placing a small-diameter metal rod between the walls 41 and 42 prior to making the peripheral weld 14, then in making the peripheral weld 14 over the entire periphery of the receptacle 1 as though there were no passage 43 to be left. Once the rod has been removed, the desired passage 43 is left behind while the remainder of the walls 41 and 42 involved in the welding imparts a certain amount of stiffness to the valve 4.

This stiffness is useful in enabling it to operate as a non-return valve. For example, to inflate the cushion 13, the patient may place an end piece (not shown) in the portion of the valve 4 that is outside the cushion and then blow into the end piece. Air penetrates through the passage 43 into the cushion 3. When the patient stops blowing, the stiffness of the valve 4 causes the walls 41 and 42 to press against each other under the effect of the pressure that exists within the cushion 3 because it has been inflated. This closes the valve in airtight manner so the cushion 3 does not deflate when the patient withdraws the end piece from the valve 4.

The patient can nevertheless provoke deflation. This can be done merely by acting on the portion of the valve 4 lying inside the cushion to separate the two walls 41 and 42 that are otherwise held pressed together by the pressure in the cushion. This can be done by causing one of the walls to slide over the other by acting through the walls 11 and 12 of the receptacle. By repeating these inflation and deflation operations on the cushion, the patient can give the cushion exactly the shape of swelling desired.

The valve 4 could equally well be constituted by a rigid non-return valve (not shown) made separately, e.g. by molding. Non-return valves are commercially available. For example, some are constituted by two flat pieces that are symmetrical to each other about the opening plane of the valve and that are pressed against each other when the valve is closed. Their section perpendicular to the plane has an end in the form of a finely tapering chamfer. It is the chamfered end that should be inserted into the cushion 3. It is sufficiently flexible that once the cushion 3 has been inflated, the pressure therein holds the two pieces pressed against each other in the same manner as the walls 41 and 42 of the above-described valve.

The person skilled in the art will be able to devise other non-return valves that could be used for the purpose of enabling the patient to inflate and deflate the padding cushion 3 of the collecting bag. It is not essential for them to be suitable for being operated by blowing therein. Other means of injecting air, e.g. a syringe, come within the present invention. It is not essential for the injected gas to be air, although air would appear, a priori, to be the most convenient.

The collecting bags shown in FIG. 3 and in the following figures differ from the embodiment described above only in the structure of the cushion 3, so the following description relates only to that element.

Figure 3:
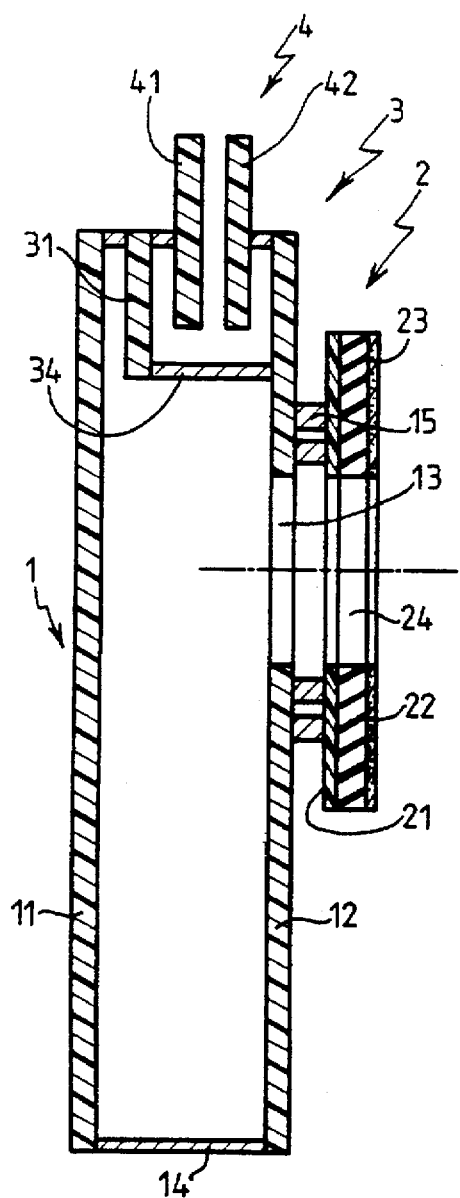
FIG. 3 is a section similar to FIG. 2 as to orientation and use of an exploded view, but it shows a variant of the embodiment of the preceding figures.

The variant shown in section in FIG. 3 has only one wall 31 for the cushion 3. This wall is welded directly to the back wall 12 of the receptacle 1 along the bottom weld 34 of the cushion. When the cushion 3 is inflated, a relatively unattractive groove is indeed formed around the weld 34. However, once the bag is in place against the patient's abdomen, it can hardly be seen. Nevertheless, a wall 32 is saved, and that may be advantageous in terms of manufacturing costs.

Figure 4:
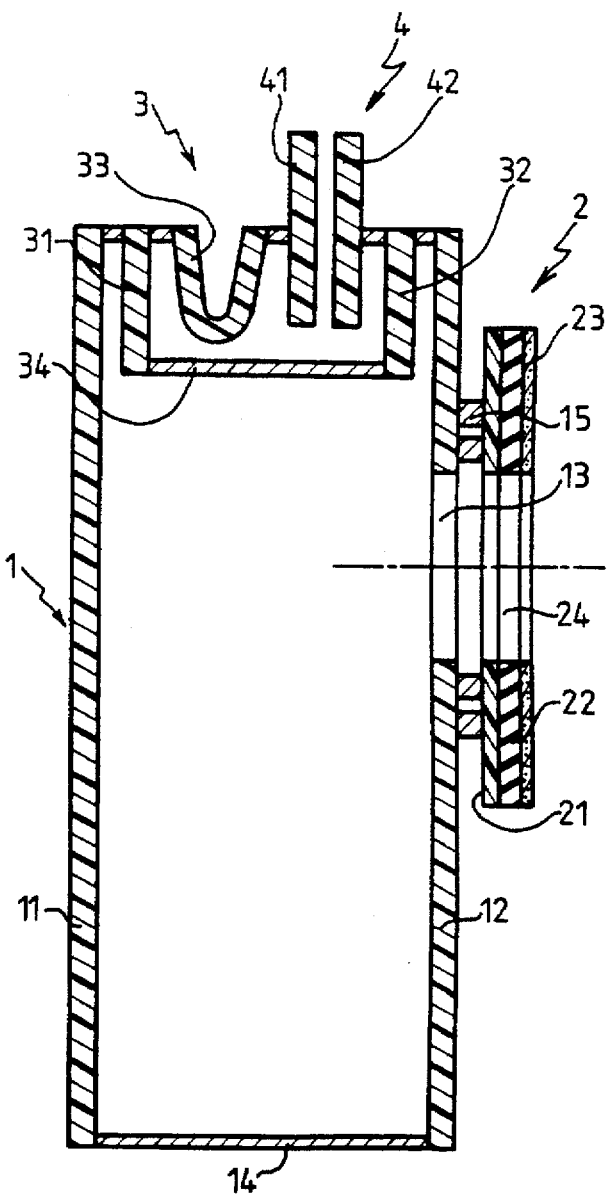
FIG. 4 is a section similar to those of FIGS. 2 and 3, both with respect to orientation and to being shown as an exploded view, however it shows another variant of the embodiment of the preceding figures.

The variant shown in section in FIG. 4 has a bellows 33 which may be made out of a strip of plastics material identical to that forming the walls 31 and 32 of the cushion with the two edges thereof being engaged in the peripheral weld 14. The corresponding cushion can achieve a much larger volume on being inflated than in the previously-described variants. Some patients seeking particularly thick padding will find such cushions advantageous.

Figure 6:
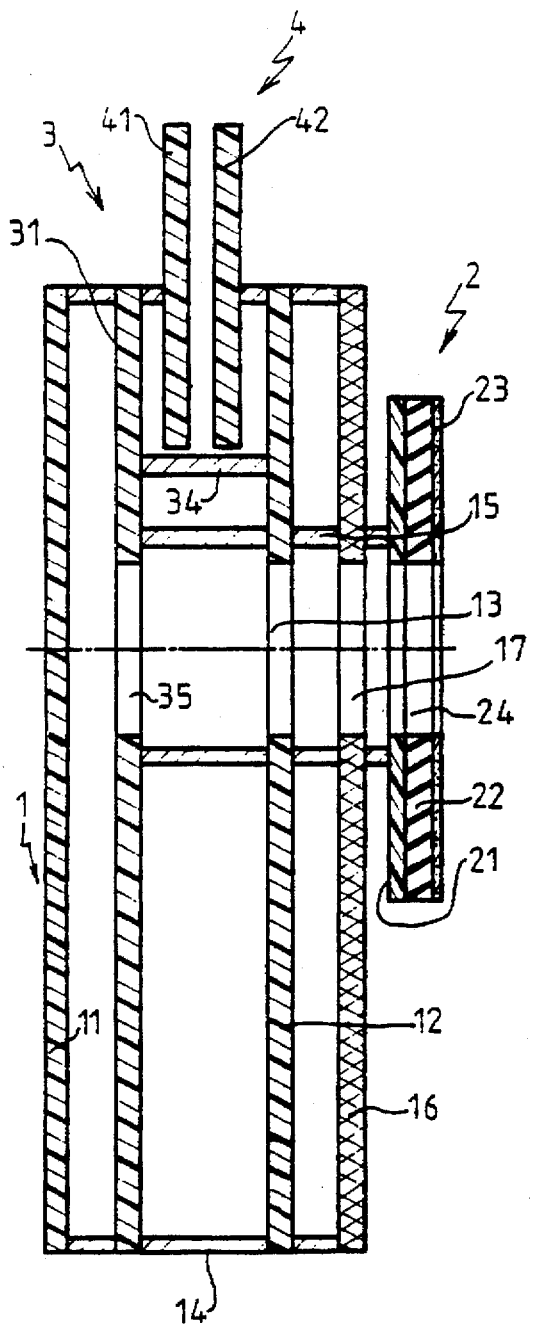
FIG. 6 is a section on the axis of symmetry I—I through the bag embodiment shown in FIG. 5, again the section is an exploded view.
Figure 5:
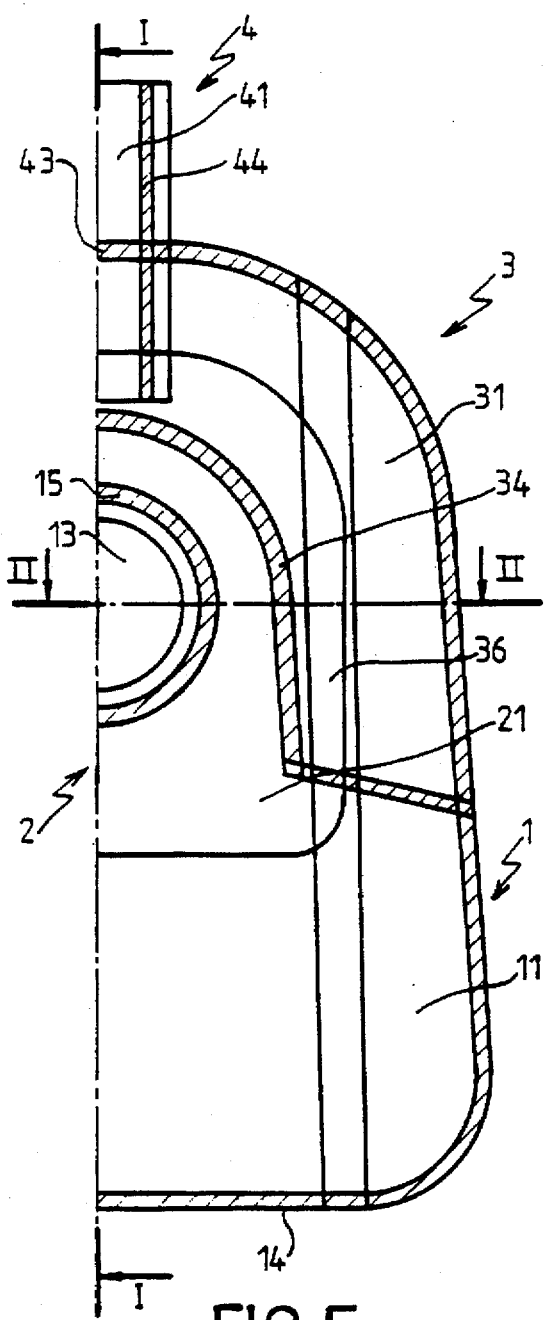
FIG. 5 is a fragmentary front view of a second embodiment of a collecting bag of the invention, and like FIG. 1 only half the bag is shown, with the non-drawn half being symmetrical about the axis I—I of the half shown.
Figure 7:
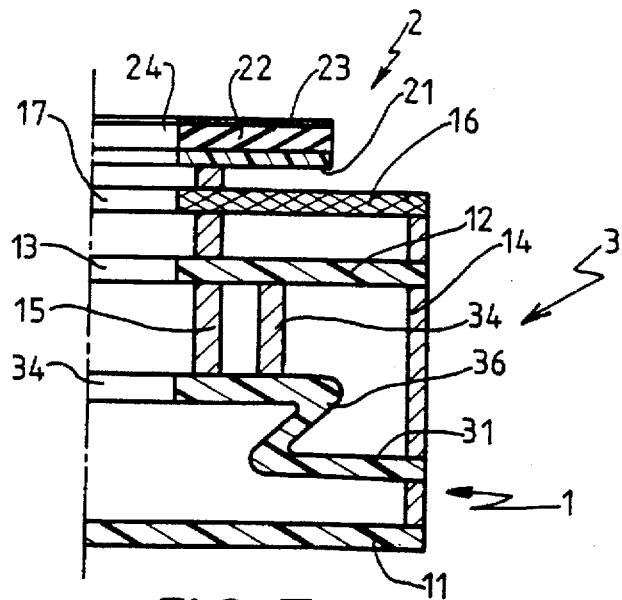
FIG. 7 is a section on axis II—II (see FIG. 5) through the bag embodiment of FIG. 5, the section is again an exploded view.

A second embodiment of the collecting bag of the invention is shown in part in a front view of FIG. 5 and in exploded sections in FIGS. 6 and 7. Like the variant of FIG. 3, there is only one wall 31 for the cushion 3, which wall is welded directly to the back wall 12 via the weld 34. However, unlike the variant of FIG. 3, the wall 31 occupies the entire surface area of the receptacle 1 of the bag. In other words it constitutes an intermediate wall which is also welded to the front and back walls 11 and 12 around the entire peripheral weld 14. To prevent it defining two separate chambers within the receptacle, it is finally welded to the back wall 12 and also to the the optional coating 16 at the weld 15 surrounding the inlet openings 13 and 17 for matter. It itself includes an opening 35 to be put in register with the other openings so that matter is stored between the front wall 11 and the intermediate wall 31.

Such an intermediate wall 31 is advantageous particularly with respect to bag manufacture. With an intermediate wall it is possible:

1) to superpose the two films of plastics material constituting the back and intermediate walls 12 and 31 and then perform the weld 34, e.g. by hot pressing the two films together along the horseshoe-shaped outline shown in FIG. 5;

2) to place a base plate and a sheet of non-woven fabric on the stack made during step 1), and then make the weld 15, e.g. by hot pressing the entire stack around a circle and then cutting out the openings 24, 17, 13, and 35 respectively from the base plate 2, the coating 16, the back wall 12, and the intermediate wall 31; and 3) taking the assembly made in step 2) and placing thereon the last film to constitute the front wall 11, to interpose the walls 41 and 42 that have already been laterally welded together, so that they extend between the films which were welded together in step 1), and to insert a rod between the walls 41 and 42, after which the peripheral weld 14 can be made, and finally the periphery of the receptacle can be cut out while ensuring that the portion of the valve 4 that lies outside the cushion 3 is not damaged.

During these steps, there is no need to take care to align any walls accurately other than those which form the valve. Assembly devices capable of performing accurate alignment are complex and expensive. This therefore constitutes a significant advantage.

In order to enable the inflated cushion to achieve an appropriate padding thickness, the intermediate wall 31 advantageously includes two vertical folds 36. In the fragmentary sections of FIGS. 5 and 7, only one of the folds is visible. The section in the horizontal plane II—II shows clearly how the fold acts as a bellows. During above-described manufacturing step 1), it is easy for the film that is to constitute the intermediate wall 31 to be folded longitudinally.

Figure 8:
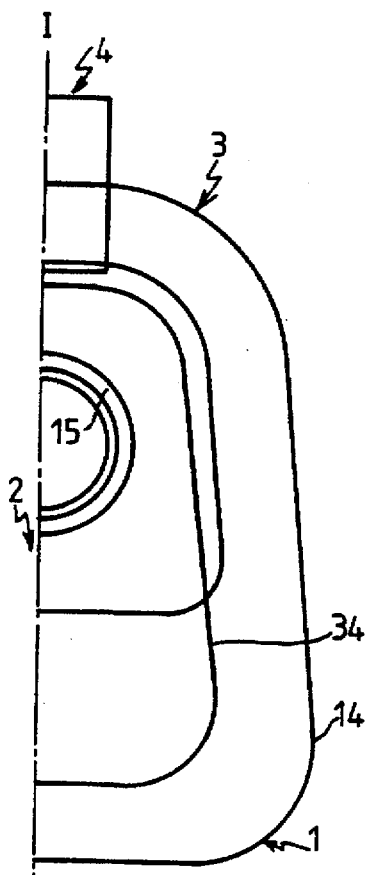
FIG. 8 is a fragmentary front view of another embodiment of the collecting bag of the invention, showing only half of the bag, and the non-drawn half thereof is symmetrical about the axis I—I.
Figure 9:
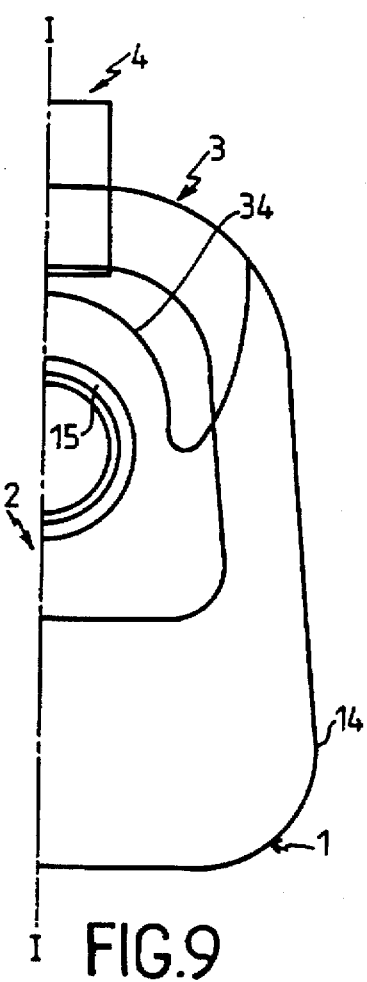
FIG. 9 is a fragmentary front view of another embodiment of the collecting bag of the invention, showing only half of the bag, and the non-drawn half thereof is symmetrical about the axis I—I.
Figure 10:
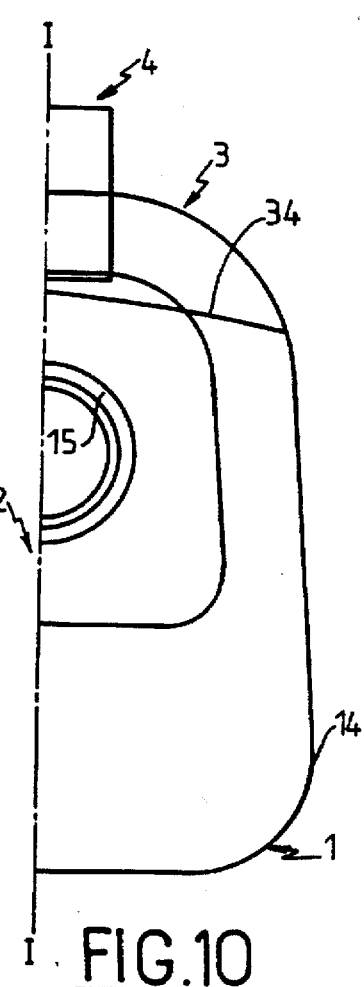
FIG. 10 is fragmentary front view of another embodiment of the collecting bag of the invention, showing only half of the bag, and the non-drawn half thereof is symmetrical about the axis I—I.

In the embodiments and variants described above, the cushion 3 is assumed to be crescent-shaped, having its bottom outline defined by the weld 34 extending parallel to the top edge of the receptacle 1 as defined by the peripheral weld 14. FIGS. 8 to 10 show other possible shapes for the cushion 3. The weld 34 may extend parallel to the weld 14 around the entire periphery of the receptacle, as shown in FIG. 8.

The weld 34 may also extend parallel to the weld 14 only in the very top portion of the receptacle as shown in FIGS. 9 and 10. In FIG. 9, it extends downwards so as to be parallel instead to the weld 15 surrounding the inlet opening for matter. In FIG. 10, the weld 34 is higher, so that the cushion is almost horizontal. Patients can choose one or other shape of bag as a function of which bag is most comfortable with the shape of their own artificial anuses.

Where appropriate, a vent filter (not shown) is disposed in known manner on the front face 11 of the receptacle 1. It is then advantageous for it to be placed in front of the wall 31 of the cushion 3. The risks of the filter being clogged by matter or being obstructed by the back wall 12 are reduced in this location. The swelling formed inside the receptacle by the cushion tends to push up the front wall.

I claim:

1. A collecting bag for collecting body excreta running from an artificial anus, said bag comprising:

a receptacle for receiving and storing said excreta, the receptacle comprising a front wall and a back wall that are welded together along a peripheral weld which defines the periphery of said receptacle, the back wall comprising an inlet opening for excreta and means for fixing the bag to the patient in such a manner that said inlet opening is in register with the artificial anus of said patient, an inflatable cushion configured to prevent pressures exerted on the bag, once placed on the patient, from bearing against the artificial anus, the cushion extending radially from the periphery of the receptacle and situated at a sufficient distance from said inlet opening such that, once the bag is placed on the patient, said cushion transmits no pressure to the artificial anus of said patient, and means for inflating said cushion, said means comprising a valve having a first end outside the cushion and a second end inside the cushion.

2. The bag according to claim 1, wherein the means for inflating the cushion also enable deflation of said cushion.

3. The bag according to claim 2, wherein the means for inflating the cushion comprise a non-return valve having at least a portion inside the cushion.

4. The bag according to claim 3, wherein the non-return valve also has an outside portion configured to receive an end piece, enabling a user to blow air therein for the purpose of inflating the cushion.

5. The bag according to claim 4, wherein the non-return valve is formed by two walls that are flexible and impermeable to gas, that face each other, that are welded together laterally, and that are provided with means for stiffening the walls of the non-return valve transversely so that the walls are pressed against each other in an airtight manner under the effect of the pressure that exists inside the cushion once inflated.

6. The bag according to claim 5, wherein the means for stiffening the walls of the non-return valve transversely are constituted by a transverse weld between the walls of the non-return valve, a passage being formed through the transverse weld to provide communication between the cushion and the outside.

7. The bag according to claim 4, wherein the non-return valve is formed by two rigid pieces that terminate at the end of the non-return valve inside the cushion in a sufficiently tapering manner to enable them to be pressed against each other in an airtight manner by the pressure that exists inside the cushion once inflated.

8. The bag according to claim 1, wherein the cushion is located inside the receptacle and is constituted by two walls that are flexible and impermeable to gas, that face each other, and that are welded together at the peripheral weld and also along an inside weld following the outline of the cushion.

9. The bag according to claim 8, wherein a third wall that is flexible and impermeable to gas has both edges engaged in the peripheral weld of the receptacle so as to form a bellows making a larger inflation volume possible.

10. The bag according to claim 1, wherein the cushion is located inside the receptacle and is constituted by a wall that is flexible and impermeable to gas, that is located between the front and back walls of the receptacle and that is welded to the back wall of said receptacle at the peripheral weld and also along an internal weld following the outline of the cushion.

11. The bag according to claim 10, wherein the wall constituting the cushion is an intermediate wall of the receptacle which is welded to the front and back walls along the entire peripheral weld, and also to the back wall along an additional weld surrounding the inlet opening for excreta so that the excreta is stored solely between the front wall and the intermediate wall.

12. The bag according to claim 11, wherein the intermediate wall includes at least one fold configured to form a bellows in the cushion to make a greater inflation volume possible.

13. The bag according to claim 1, in which the receptacle, once placed on the patient, has a top portion and a bottom portion, wherein the cushion extends in at least the top portion of the receptacle.

14. The bag according to claim 13, wherein a vent filter is disposed on the front wall of the receptacle at the same height as the cushion.

15. The collecting bag for collecting body excreta running from an artificial anus, said bag comprising:

a receptacle for receiving and storing said excreta, the receptacle comprising a front wall and a back wall that are welded together along a peripheral weld which defines the periphery of said receptacle, the back wall comprising an inlet opening for excreta and means for fixing the bag to the patient in such a manner that said inlet opening is in register with the artificial anus of said patient, the receptacle having, once the bag is placed on the patient, a top portion and a bottom portion, an inflatable cushion extending in at least the top portion of the receptacle and configured to prevent pressures exerted on the bag, once placed on the patient, from bearing against the artificial anus, the cushion extending radially from the periphery of the receptacle towards the inlet opening and ending at a sufficient distance from said inlet opening so that, once the bag is placed on the patient, said cushion transmits no pressure to the artificial anus of said patient, and means for inflating the cushion, said means comprising a valve having a first end outside the cushion an a second end inside the cushion.

* * * * *